United States Patent
Ishihara (10) Patent No.: US 9,341,469 B2
(45) Date of Patent: May 17, 2016

(54) CONTINUOUS SCAN TYPE MEASURING APPARATUS

(71) Applicant: TAKAOKA TOKO CO., LTD., Koto-ku (JP)

(72) Inventor: Mitsuhiro Ishihara, Hamamatsu-shi (JP)

(73) Assignee: TAKAOKA TOKO CO., LTD., Koto-Ku (JP)

(*) Notice: Subject to any disclaimer, the term of this patent is extended or adjusted under 35 U.S.C. 154(b) by 0 days.

(21) Appl. No.: 14/564,915

(22) Filed: Dec. 9, 2014

(65) Prior Publication Data
US 2015/0204660 A1 Jul. 23, 2015

(30) Foreign Application Priority Data
Jan. 17, 2014 (JP) .................................. 2014-007092

(51) Int. Cl.
*H04N 7/18* (2006.01)
*G01B 11/25* (2006.01)
*G01N 21/95* (2006.01)

(52) U.S. Cl.
CPC ........ *G01B 11/2518* (2013.01); *G01B 11/2527* (2013.01); *G01B 2210/56* (2013.01); *G01N 21/9501* (2013.01)

(58) Field of Classification Search
CPC .................... G01B 11/2518; G01B 11/2527
USPC ........................................................ 348/135
See application file for complete search history.

(56) References Cited

U.S. PATENT DOCUMENTS

| 2009/0123874 A1* | 5/2009 | Nagayama | .......... G03F 7/70525 430/311 |
| 2011/0008717 A1* | 1/2011 | Ichinose | ............. G03F 7/70691 430/30 |

FOREIGN PATENT DOCUMENTS

| JP | 06-242016 A | 9/1994 |
| JP | 2002-280283 | 9/2002 |
| JP | 2005-030774 A | 2/2005 |
| JP | 2007-10497 | 1/2007 |
| JP | 2007-232474 A | 9/2007 |
| JP | 2011-164430 | 8/2011 |
| JP | 2013-74204 | 4/2013 |
| JP | 2013-83655 | 5/2013 |

* cited by examiner

*Primary Examiner* — Richard Torrente
(74) *Attorney, Agent, or Firm* — Oblon, McClelland, Maier & Neustadt, L.L.P (57) ABSTRACT

A continuous scan type measuring apparatus includes a continuous scan type optical application measuring instrument, a single-axis measuring instrument scanning stage and two carrier stages. The continuous scan type optical application measuring instrument performs a surface shape measurement of a measuring object. The single-axis measuring instrument scanning stage carries the optical application measuring instrument and causes the optical application measuring instrument to perform continuous scanning along a predetermined direction. The two carrier stages are detachably mount respective measuring objects thereon and move independently of each other. The two carrier stages are positioned independently at one of a measurement position within a scanning range of the optical application measuring instrument and a replacement position of the measuring objects. A carrier stage, which is at the measurement position and on which the measuring object subjected to the surface shape measurement is mounted, is fixed during the continuous scanning.

15 Claims, 6 Drawing Sheets

CONTINUOUS SCAN TYPE MEASURING APPARATUS

CROSS-REFERENCE TO RELATED APPLICATIONS

This application claims the benefit of priority of Japanese Patent Application No. 2014-007092, filed Jan. 17, 2014, the entire contents of which are incorporated herein by reference.

FIELD

Embodiments described herein relate generally to a measurement and inspection apparatus which uses light, and more particularly, to speeding up an apparatus for measuring and inspecting surface shape of a measuring object.

BACKGROUND

A panel of a high-density wiring board (hereinafter referred to simply as a board), single-piece substrates (substrates cut from a panel) arranged on a tray, wafer, or the like is used for a semiconductor product. This kind of board or the like is about 200 to 400 mm square in a planer direction for example. The microelectrodes called bumps and arranged on the board is however only about 0.02 to 0.1 mm in height and height dimension inspection of the bumps is regarded as important. Measuring accuracy required for the height inspection of the bumps is on a micron level, meaning that it is required to measure an object having a large surface area with high accuracy.

Besides, since semiconductors are mass-produced articles, markedly high speed is also required even more than high-accuracy measurement.

Two methods may be taken for taking high-speed, high-accuracy shape measurements of a surface of an object having such a large area have been put to practical use. The first method may be a method which takes measurements by using a surface shape measuring instrument of an area measurement type and moving the object or measuring instrument step by step (hereinafter referred to simply as a step scanning type). The second method may be a method which takes measurements by using a surface shape measuring instrument of a linear measurement type and continuously scanning the object or measuring instrument (hereinafter referred to simply as a continuous scan type).

The step scanning type, which uses the surface shape measuring instrument of the area measurement type, does not require any step movement as long as the entire object fits in an area size, i.e., a field-of-view size. However, when high-accuracy measurement is required, it is difficult for the measuring instrument to have a sufficiently wide field-of-view size due to constraints of an optical system and constraints of a resolution of a two-dimensional detector. Consequently, as the field-of-view size is generally a few millimeters square to a few tens of millimeters square, it is necessary to piece together measurements taken in a large number of fields of view via step movements.

In the case of step movements, it is necessary to move fast and stop quickly for high-speed measurement. The vibrations during acceleration and deceleration affect measuring accuracy, making it necessary to increase apparatus rigidity and resulting in size and cost increases of the apparatus.

Meanwhile, in the case of the continuous scan type, velocity stability and high linearity are required of a movable stage, but there is not much acceleration and deceleration, and thus high-speed movement can be achieved without incurring size and cost increases. Thus, it can be said that the continuous scan type is superior as a method for performing shape measurement of an object having a large area with high accuracy at high speed.

As a surface shape measuring technique of the continuous scan type, a light section method is used commonly. The light section method which is based on a principle that, when linear pattern is projected onto an object and a straight light beam projected from a direction different from a projection direction of the linear pattern is observed on an image, a straight line appears distorted according to undulation of the object, is a technique for measuring an amount of distortion on the image and thereby measuring the undulation, i.e., surface shape. One line of surface shape on the linear pattern can be measured from one image, and by acquiring images continuously while moving the movable stage continuously, it is possible to measure the surface shape of the object seamlessly.

However, even though the entire object can be measured in a scanning direction, in a direction orthogonal to the scanning direction, since scanning is limited by the field-of-view size of the image, each time a scan is finished, a scan may be carried out again by moving one field of view using the movable stage having an axis orthogonal to the scanning direction, and this may be repeated until scanning of the entire object is finished. That is, movements along two axes are necessary using a stage along a scanning axis and a stage along a field-of-view movement axis.

Figure 7:
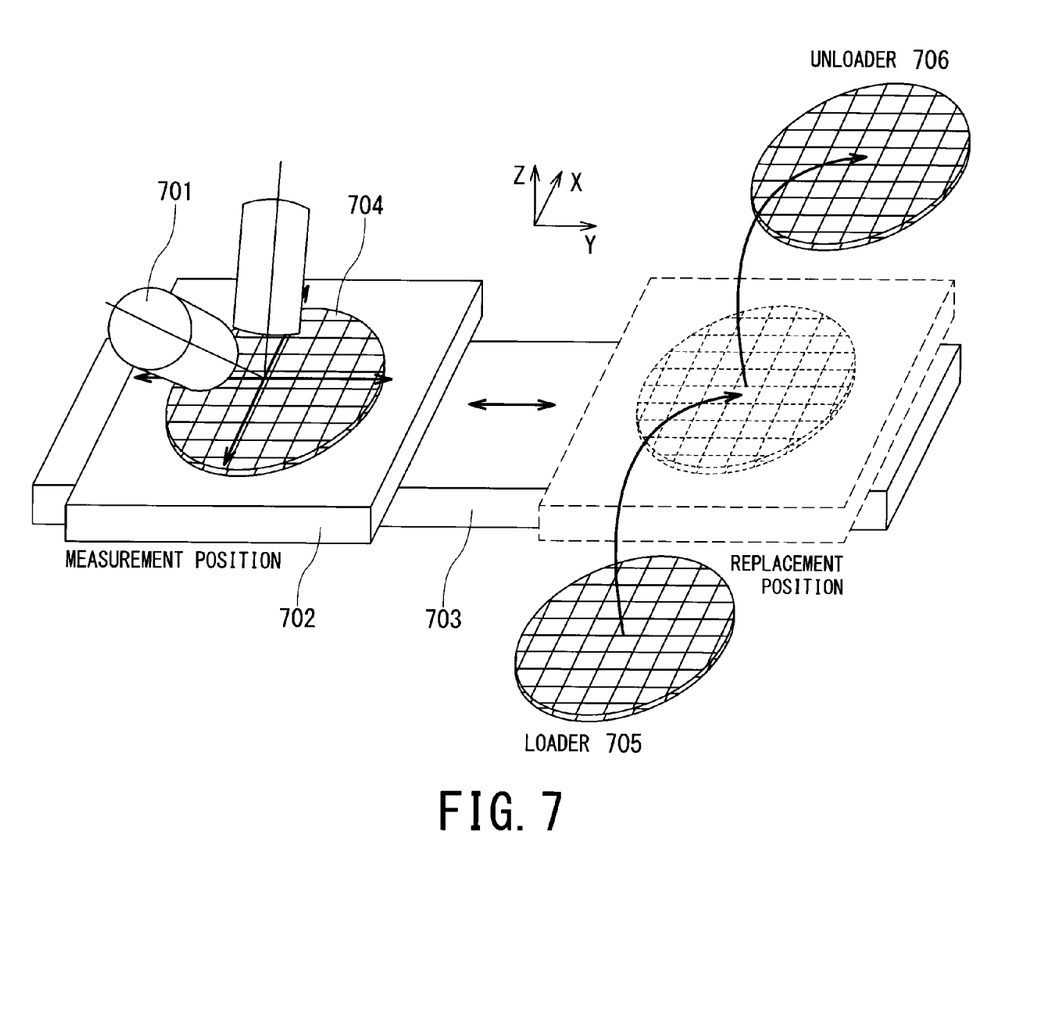
FIG. 7 is a diagram for describing a conventional technique.

With a typical inspection apparatus, a measuring object is mounted on an XY stage and measurements are taken by scanning the XY stage. A configuration of a typical inspection apparatus is shown in FIG. 7. When a measuring object 704 is a mass-produced article such as a semiconductor product, a large quantity of the measuring objects 704 needs to be measured and it is necessary to take measurements by replacing the measuring objects 704 one after another. Therefore, transport apparatus (loader 705 and unloader 706) are provided to replace the measuring object 704 on an XY stage 702 and a Y-axis stage 703. Typical operation will be described below.

When the measuring instrument 701 completes the measurement of the measuring object 704 on the XY stage 702, an elongate Y-axis stage 703 moves to a location where the measuring object 704 can be replaced without interfering mechanically with the measuring instrument during the replacement. Subsequently, the product already measured is removed by the transport apparatus and a product yet to be measured is placed, positioned, and fixed on the XY stage 702 and 703. The product is moved to an original position under the measuring instrument by the Y-axis stage 703 and measurement is started again. This operation is repeated.

Inspection of mass-produced articles requires high rapidity. Therefore, a surface shape measuring instrument of the continuous scan type advantageous to high-speed measurement is used as described above. However, even if high-speed measurement is achieved, if it takes time to replace the product on the XY stage, this cannot be said to be a high-speed inspection when all things are taken into consideration.

It can be said that product replacement time, which not only affects apparatus speed, but also keeps the measuring instrument idle, creates an uneconomical situation in which the expensive measuring instrument is not fully utilized.

Also, although the light section method is used as a surface shape measuring technique of the continuous scan type, since only one line of surface shape measurement results is obtained from one image, the light section method cannot be said to be an effective technique actually. To compensate for such inefficiency, measures are taken to improve efficiency, such as increasing image sensing speed of an image sensing device and processing images using a dedicated electronic circuit installed near the image sensing device without transferring the images to a computer, though such special development is desirably be unnecessary if possible. The efficiency can be said to be poor also in terms of development efficiency.

Furthermore, detection of a center position of the linear pattern by the light section method is considered to be affected by surface conditions of the object in principle, and thus it cannot be said that reliability of measurement is high. Furthermore, a laser beam normally used as linear pattern becomes a major error factor in center position detection because the laser beam is prone to speckles which produce an unnatural intensity distribution in the image formed on the image sensing device.

SUMMARY

The present invention has been made in light of the above situation, and it is an object of the present invention to provide a continuous scan type measuring apparatus for increase efficiency and speed of the apparatus as a whole.

To solve the above-described issues, a continuous scan type measuring apparatus according to an aspect of the present invention includes a continuous scan type optical application measuring instrument, a single-axis measuring instrument scanning stage and two carrier stages. The continuous scan type optical application measuring instrument performs a surface shape measurement of a measuring object. The single-axis measuring instrument scanning stage carries the optical application measuring instrument and causes the optical application measuring instrument to perform continuous scanning along a predetermined direction. The two carrier stages are detachably mount respective measuring objects thereon and move independently of each other. The two carrier stages are positioned independently at one of a measurement position within a scanning range of the optical application measuring instrument and a replacement position of the measuring objects. One of the two carrier stages, which is at the measurement position and on which the measuring object subjected to the surface shape measurement is mounted, is fixed during the continuous scanning. The optical application measuring instrument performs, while the measuring object which has been measured is being replaced with a next measuring object with one of the two carrier stages positioned at the replacement position, the surface shape measurement of the measuring object on the other of the two carrier stages positioned at the measurement position. The measuring instrument scanning stage causes the optical application measuring instrument to perform continuous scans repeatedly along the predetermined direction at intervals of a predetermined waiting time when a measurement width covered by the optical application measuring instrument in a direction orthogonal to the predetermined direction is smaller than a width of the measuring object in the orthogonal direction. When continuous scans are performed repeatedly, the carrier stage, which is at the measurement position and on which the measuring object subjected to the surface shape measurement is mounted, is fixed during the continuous scanning, and moves in the orthogonal direction by a width equal to or smaller than the measurement width in the orthogonal direction during the predetermined waiting time.

With the continuous scan type measuring apparatus, it is possible to increase efficiency and speed of the apparatus as a whole.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of a continuous scan type measuring apparatus according to embodiments of the present invention with reference to the drawings.

Figure 1:
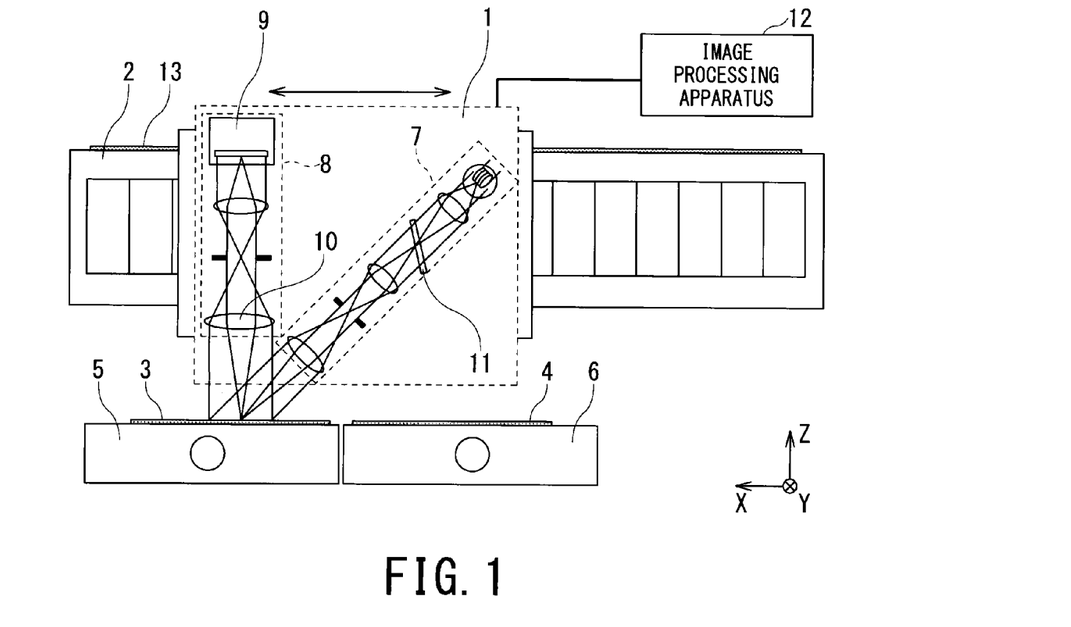
FIG. 1 is a front view of an example of an apparatus according to an embodiment of the present invention.

As shown in FIG. 1, a continuous scan type measuring apparatus 100 according to an embodiment of the present invention includes an optical application measuring instrument 1, a single-axis measuring instrument scanning stage 2 carrying the optical application measuring instrument 1, and a pair of carrier stages 5 and 6 on which measuring objects 3 and 4 are mounted, respectively. Note that the continuous scan type measuring apparatus 100 may further include one or more carrier stages in addition to the carrier stages 5 and 6.

The optical application measuring instrument 1 is a measuring instrument of a continuous scan type and is configured to measure the measuring objects 3 and 4 carried by the carrier stages 5 and 6 while being moved by the measuring instrument scanning stage 2 at constant speed. The carrier stages 5 and 6 are single-axis stages of same specifications and are configured to be able to move independently of each other along a direction (hereinafter referred to as a Y direction) orthogonal to a scanning direction (hereinafter referred to as an X direction) of the optical application measuring instrument 1.

By moving in the Y direction, the carrier stages 5 and 6 are positioned at one of two positions: a measurement position within a scanning range in the X direction of the optical application measuring instrument 1 and a replacement position (object replacement position) of the measuring objects 3 and 4. Also, it is assumed that a Y-direction width of the measurement position at which the carrier stages 5 and 6 are positioned is larger than a Y-direction width of the measuring objects 3 and 4.

That is, when the optical application measuring instrument 1 cannot measure the measuring objects 3 and 4 by a single scan, the carrier stages 5 and 6 serves a role of moving the measuring objects 3 and 4 by a width (e.g., a width of just one field of view) equal to or smaller than the width of one field of view (measurement width in the Y direction the optical application measuring instrument 1 can cover by one continuous scan) in the Y direction within the Y-direction width of the measurement position, and thereby causing the optical application measuring instrument 1 to perform continuous scans repeatedly along the X direction such that the entire surfaces of the measuring objects 3 and 4 can be measured. The carrier stages 5 and 6 as well as serves a role of moving the measuring objects 3 and 4 to the object replacement position where the measuring objects 3 and 4 will not mechanically interfere with the optical application measuring instrument 1 when the objects 3 and 4 are replaced.

Regarding the measurement position where the carrier stages 5 and 6 are positioned, the carrier stages 5 and 6 may share a same position or use positions different from each other. When the same position is shared, a scanning range of the optical application measuring instrument 1 in the X direction can be made narrower than when positions different from each other are used. In an example described below, the measurement positions at which the carrier stages 5 and 6 are positioned differ from each other, run along the X direction, and fall within the scanning range of the optical application measuring instrument 1 in the X direction so that while the measuring object mounted on one of the carrier stages 5 and 6 is being replaced, the measuring object mounted on another carrier stage can be scanned easily.

The replacement positions where the carrier stages 5 and 6 may be positioned can be such that the measuring objects 3 and 4 will not mechanically interfere with the optical application measuring instrument 1. For example, the replacement positions may be positions along a direction (including the Y direction and a Z direction) intersecting the measurement positions in the X direction. Also, the replacement positions may be located along the measurement positions in an X-axis direction and fall outside a movement range of the optical application measuring instrument 1.

Movement axes of the carrier stages 5 and 6 do not need to be uniaxial, and when moving between the replacement position and measurement position, the carrier stages 5 and 6 may move linearly, perform a combination of linear movements, or move curvilinearly. Also, plural replacement positions may be provided and one of the replacement positions may be selected as appropriate. When plural replacement positions are provided, the loader 705 and unloader 706 may be installed at each of the plural positions.

An example in which a replacement position is aligned with respect to a measurement position in the Y direction will be described below.

Figure 2:
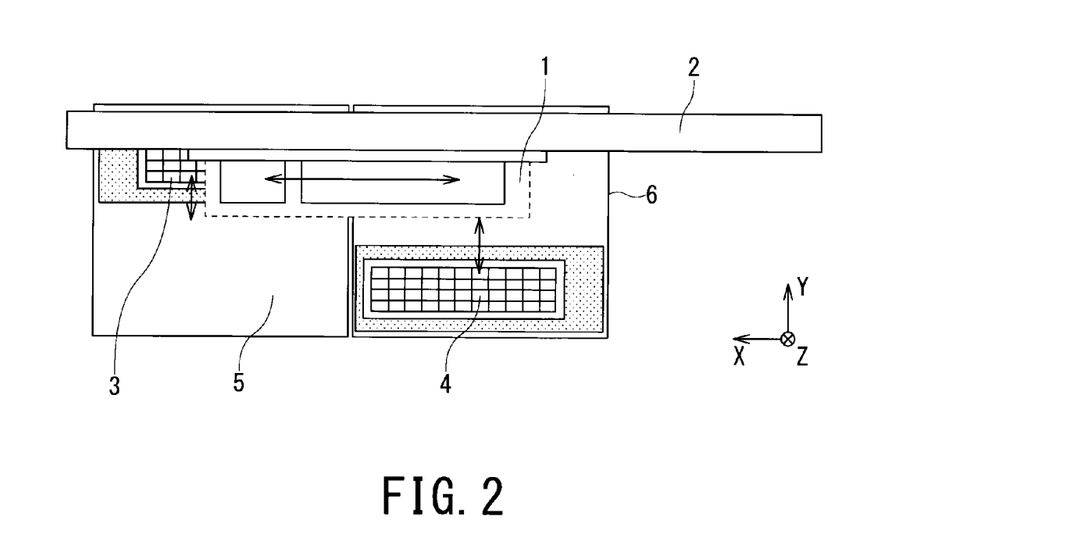
FIG. 2 is a top view of an example of an apparatus according to an embodiment of the present invention.

Overall operation will be described with reference to FIG. 2, which is a top view of the apparatus in FIG. 1.

It is assumed that each of the measuring objects 3 and 4 is elongate in the X direction and has a width equal to or smaller than two fields of view of the optical application measuring instrument 1 in the Y direction. That is, the measuring object is sized such that the measurement of the entire surface can be completed by two scans with the optical application measuring instrument 1. Of semiconductor package substrates, such elongate substrates are called strip substrates and have recently come into widespread use as IC package substrates for mobile devices.

A measurement start condition is regarded as a condition in which the optical application measuring instrument 1 is located at a midpoint position between the two carrier stages 5 and 6, the carrier stage 6 is positioned at the measurement position, and the optical application measuring instrument 1 is moving toward the measuring object 4 on the carrier stage 6. If the Y-direction width of the measuring objects 3 and 4 is larger than one field of view (measurement width) of the optical application measuring instrument 1, advisably initial positions of the measurement positions at which the carrier stages 5 and 6 are positioned are such that one field of view from end portions of the measuring objects 3 and 4 in the Y direction can be measured.

The optical application measuring instrument 1 measures half the measuring object 4 in the Y direction by moving along the X direction until an end of the measuring object 4 is reached and then stops for a predetermined waiting time. During continuous scanning in the X direction, the carrier stage 6 is fixed. Next, as the carrier stage 6 on which the measuring object 4 undergoing surface shape measurement is mounted moves, for example, by one field of view in the Y direction from the current measurement position, placing the measuring object 4 in another half of the measurement position in the Y direction, the optical application measuring instrument 1 starts scanning in a reverse orientation along the X direction to measure a remaining half of the measuring object 4. If the Y-direction width of the measuring object 4 is still larger, continuous scanning in the X direction can be repeated after the carrier stage 6 moves, for example, by one field of view in the Y direction from the current measurement position during the predetermined waiting time.

When the optical application measuring instrument 1 reaches an original position, i.e., the midpoint position between the carrier stages 5 and 6, the measurement of the measuring object 4 is complete, and thus the carrier stage 6 moves in the Y direction to the measuring object replacement position, replaces the measuring object 4 with a next one, and returns to the original measurement position by carrying the new measuring object 4.

While the carrier stage 6 is replacing the measuring object 4 with the next one, the optical application measuring instrument 1 simply goes on measuring the measuring object 3 through continuous movement without stopping at the midpoint position between the carrier stages 5 and 6. As in the case of the measuring object 4, the optical application measuring instrument 1 measures all surfaces of the measuring object 3 through reciprocating action along the X direction and reaches the midpoint position between the carrier stages 5 and 6.

At this point, if the carrier stage 6 has returned to the measurement position by completing a replacement operation of the measuring object 4, the optical application measuring instrument 1 can just keep on moving along the X direction without stopping and measure the new measuring object 4.

While the new measuring object 4 is being measured, the carrier stage 5 is positioned first at the replacement position by moving along the Y direction and then returns to the original measurement position by moving along the Y direction again after replacement operation of replacing the measuring object 3 already measured to a next, new measuring object 3.

As described above, if the measuring object replacement time is shorter than the time during which one of the measuring objects undergoes reciprocating measurements, the optical application measuring instrument 1 can measure the measuring objects 3 and 4 by ceaselessly continuing a simple reciprocating operation for a distance a little longer than X-direction size of the two measuring objects.

This is an efficient technique because the optical application measuring instrument 1 can be operated ceaselessly as well as a high-speed technique which can reduce cycle time of the apparatus because the measuring object replacement time can be practically ignored.

If the replacement time of the measuring object is longer than the reciprocating measurement time, such as when the size of the measuring objects 3 and 4 is very small, it becomes necessary for ceaseless measuring to take measures such as increasing the reciprocating measurement time by adjusting speed of the measuring instrument scanning stage 2, which makes it difficult to use capabilities of the measuring instrument effectively. However, since originally a purpose of the present embodiment is to measure measuring objects having a large area, it can be said that such a situation is out of scope.

Although in the operation example above, it is assumed that the entire measuring object is measured by one reciprocating operation, i.e., by two scans, performed by the optical application measuring instrument 1, the measurement is not limited to one reciprocation and any number of reciprocations may be used. However, efficient measurement without waste requires an even number 2N of scans (N reciprocations). For example, a Y-size measuring object which can be measured by three fields of view (three scans) produces wasted time corresponding to one scan.

The optical application measuring instrument 1 can be a measuring instrument or tester of the continuous scan type, and is not limited to a surface shape measuring instrument such as described below. For example, an image tester is capable of acquiring and analyzing images through instantaneous exposure using a shutter or stroboscope while performing continuous scanning. Examples of the optical application measuring instrument 1 according to the present embodiment include many other non-contact measuring instruments and testers.

Next, an example in which the optical application measuring instrument 1 is a surface shape measuring instrument of the continuous scan type will be shown. As described in relation to the conventional technique, a measuring instrument using the light section method is a typical example of the surface shape measuring instrument of the continuous scan type, but it cannot be said that the light section method excels in either efficiency or reliability as a surface shape measuring instrument.

An embodiment of the optical application measuring instrument 1 according to the present invention will be described with reference to FIGS. 1 to 5.

Figure 3:
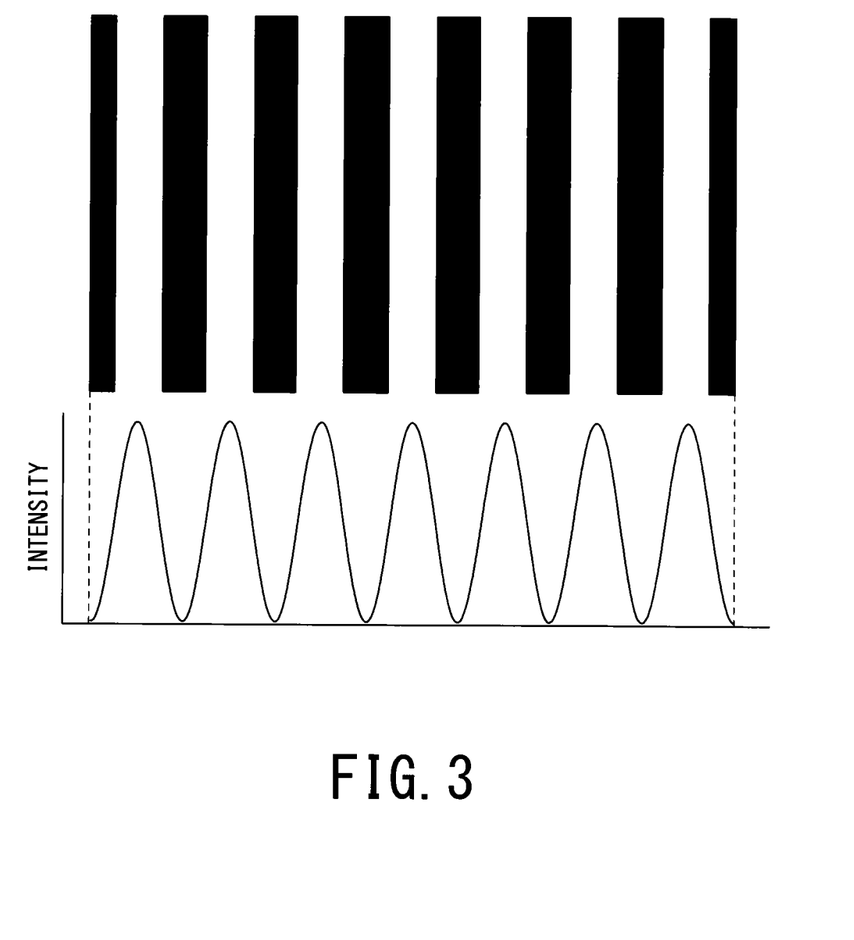
FIG. 3 is an explanatory diagram for describing an example of a grating pattern.

The optical application measuring instrument 1 is a surface shape measuring instrument based on a grating projection phase shift method and is designed such that a multi-slit sinusoidal grating pattern such as shown in FIG. 3 will be projected onto the measuring object 3 by a grating projection unit 7. The grating projection unit 7 is a telecentric optical system and is designed such that projected grating period will not change even if a Z-direction position of the measuring object 3 changes.

Although in the example described below, the measuring objects 3 and 4 are mounted on the carrier stages 5 and 6, respectively, if the optical application measuring instrument 1 is a grating projection type surface shape measuring instrument of the continuous scan type and continuous scanning is achieved by movement of the optical application measuring instrument 1, typical fixed stages for mounting measuring objects may be used instead of the carrier stages. Even when fixed stages are used, if continuous scanning is performed through movement of the optical application measuring instrument 1, which is a grating projection type surface shape measuring instrument efficiency and speed of the apparatus can be improved more fully as a whole than when the light section method is used.

The projected grating pattern is photographed by an image sensing unit 8 having an optical axis at an angle different from that of the grating projection unit 7. The image sensing unit 8 includes a two-dimensional image sensing device, such as a CMOS area sensor 9, which is a two-dimensional arrangement of electromagnetic wave-electricity conversion elements configured to convert an electromagnetic wave into an electrical signal, and an image forming lens 10 which is an image forming unit configured to form an image of the measuring object 3 on the CMOS area sensor 9. The image forming lens 10 is also a telecentric lens.

Although the optical axis of the image sensing unit 8 is placed perpendicular to a mounting surface of the carrier stages 5 in FIG. 1, if the measuring object 3 has surface properties such as low surface roughness and reduced scattering, there is a possibility that a reflected light from the measuring object 3 might not be incident on the image sensing unit 8. In such a case, advisably the optical axis of the grating projection unit 7 and optical axis of the image sensing unit 8 are angled to be nearly symmetrical to each other with respect to a normal to a measuring surface of the measuring object 3 in order to sense images under light closer to specularly reflected light.

In that case, a problem can arise in that an image obtained by the image sensing unit 8 is distorted or focus differs between near side and far side, and so the CMOS area sensor 9 is placed at an angle with the optical axis (tilt-shift structure). The grating projection unit 7, if configured as shown in FIG. 1 to form an image of a real lattice 11, is preferably tilted-shifted similarly.

A video signal obtained by the CMOS area sensor 9 is sent to an image processing apparatus 12 and is subjected to calculations on a pixel by pixel basis.

A plane containing an optical axis of the image forming lens 10 and optical axis of the grating projection unit 7 is placed so as to be parallel to a movement axis, i.e., X-axis of the measuring instrument scanning stage 2. Also, the measuring instrument scanning stage 2 is equipped with a linear encoder 13 to keep track of position accurately at high speed during movement. Feedback control by means of a linear motor and the linear encoder 13 makes it possible to configure a scanning stage of precise constant speed.

Another encoder may be used as long as the position of the measuring instrument scanning stage 2 can be kept track accurately at high speed, or in extreme cases, use of such an encoder could be eliminated. For example, if accurate speed control is possible in some way, the stage position can be kept track accurately based on travel time and the encoder becomes unnecessary.

A method for implementing measurement based on the grating projection phase shift method by consecutively moving in the X-axis direction using an apparatus of the above configuration will be described in detail below. A 3-step phase shift method (technique which uses three images), which is the simplest method, will be described below as an example, but any number of steps larger than three are applicable.

Figure 4:
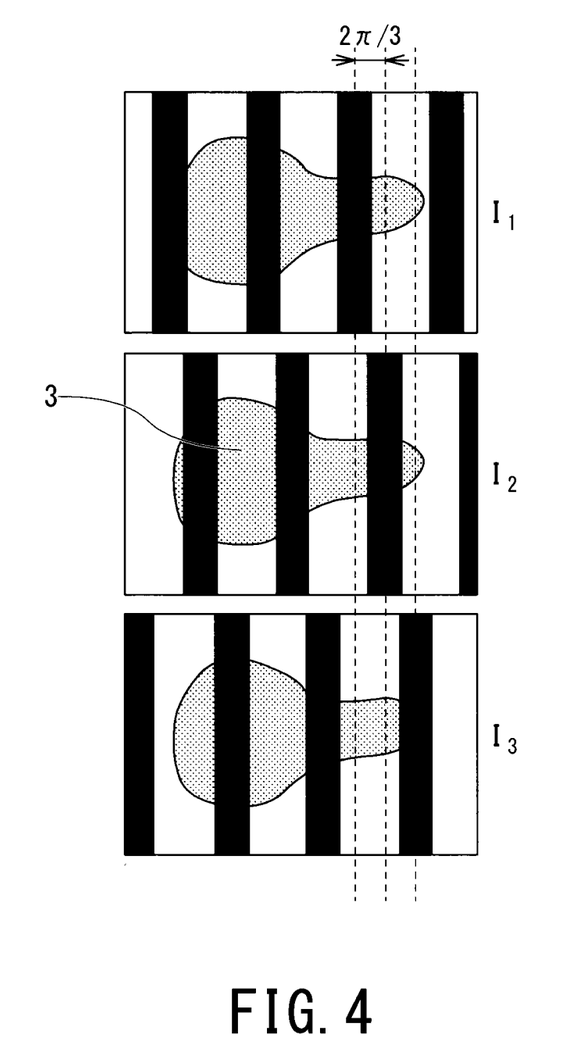
FIG. 4 is a diagram for describing a conventional grating projection phase shift method.

First, a typical (conventional) grating projection phase shift method will be described briefly. FIG. 4 is an example in which four grating lines are projected in one field of view (one imaging area of the CMOS area sensor 9). Although a black-and-white binary grating pattern is illustrated, actually it is assumed that the grating has a sinusoidal pattern in which light and shade change sinusoidally as in the case of FIG. 3. If the measuring object 3 is not flat, distortion occurs in the grating pattern, and the distortion indicates nothing less than height, but a distortion-free pattern is shown here for convenience' sake. The following discussion is not affected by the presence or absence of distortion, i.e., the presence or absence of undulation on the measuring object 3. I1, I2, and I3 in FIG. 4 show images projected by shifting a phase of the grating by $2\pi/3$ each. In so doing, values I1(x,y), I2(x,y), I3(x,y) of the respective images at same coordinates (x,y) represent points on a sine wave differing from each other by $2\pi/3$, and an initial phase $\phi$ of the sine wave can be determined as follows.

$$\phi(x,y) = \arctan[\sqrt{3}*(I1(x,y)-I3(x,y))/(2*I2(x,y)-I1(x,y)-I3(x,y))]$$

More generally, if a phase shift amount is $\phi=2\pi/N$ when an N-step phase shift method is used, the initial phase $\phi$ is determined as follows.

$$\phi(x,y) = \arctan[-\Sigma Ii(x,y)\sin(i\phi)/\Sigma Ii(x,y)\cos(i\phi)]$$
$$(i=0,1,\ldots,N-1)$$

By performing a similar calculation at every coordinate point (x,y) the initial phase can be determined for every pixel. For example, when the measuring object is flat, points of a same initial phase, when linked together, draw a single straight line (hereinafter referred to as an equiphase line). The equiphase line becomes deformed and distorted when the measuring object is undulated and thereby acquires undulation information, allowing height to be measured. This is based on exactly the same principle as the light section method. That is, the equiphase line of the initial phase is considered to be identical with a center line of the linear pattern of the light section method. Whereas the light section method can obtain height measurement data for only one center line of the linear pattern from one image, the grating projection phase shift method can obtain all the height measurement data in images from at least three images after all because the method can determine the initial phases of all points in the images and also because the initial phase enables height measurement. Based on the above, the grating projection phase shift method according to the present invention will be described with reference to FIG. 5.

Figure 5:
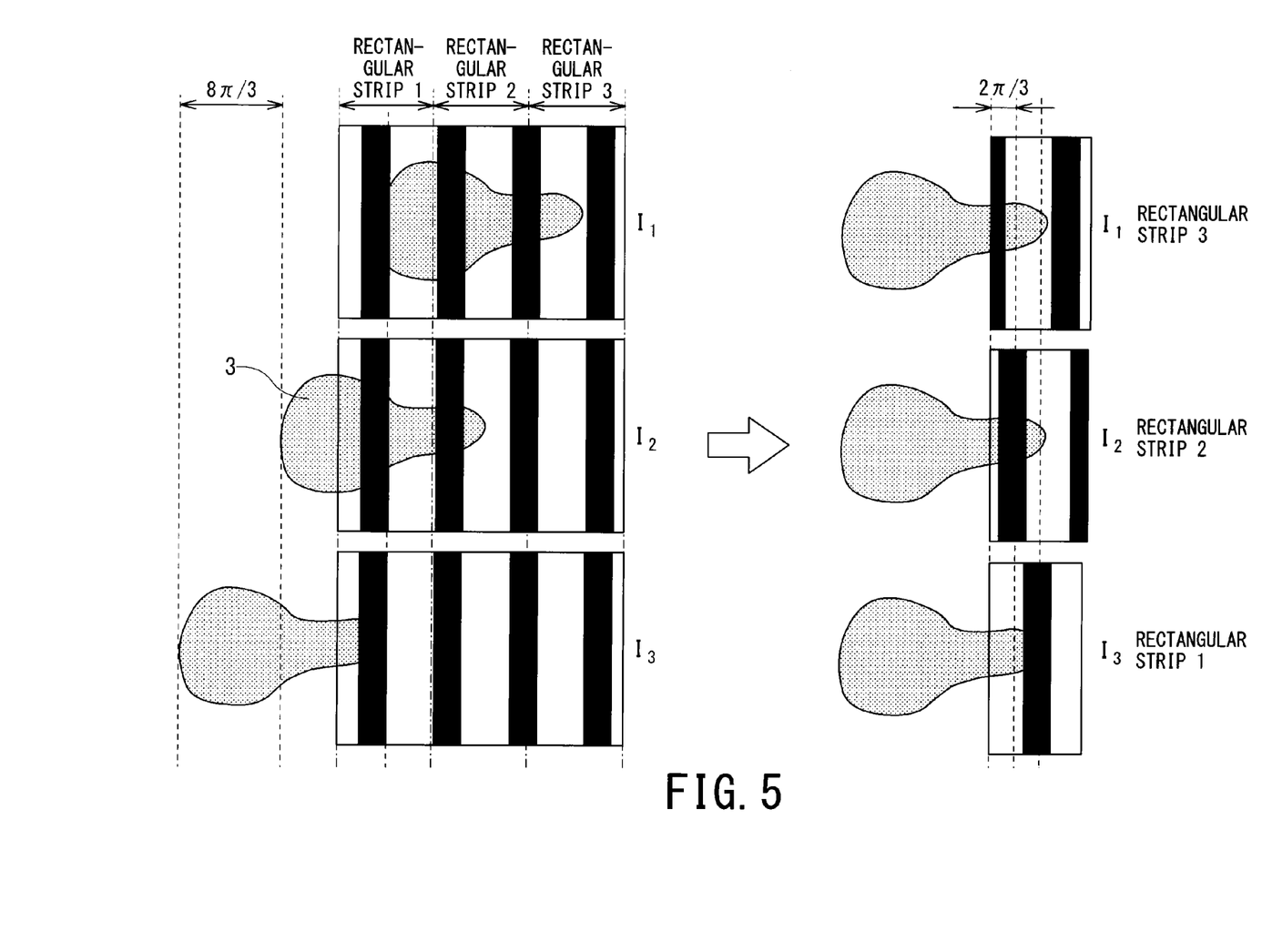
FIG. 5 is an explanatory diagram for describing an example of the grating projection phase shift method according to the present invention.

It is assumed that an image shown in I1 of FIG. 5 is obtained by releasing a shutter of the CMOS area sensor 9 with certain timing when the measuring instrument scanning stage 2 is moving at constant speed. This is equivalent to I1 of FIG. 4. Then, when the shutter is released again after the measuring instrument scanning stage 2 moves by 4/3 (=1+1/3) the projected grating period ($8\pi/3$ in terms of the phase), an image shown in 12 of FIG. 5 is taken. Furthermore, an image shown in 13 of FIG. 5 is obtained when the shutter is opened after a same time interval (i.e., after the measuring instrument scanning stage 2 further moves by 4/3 the grating period). Subsequently, images are acquired one after another by opening the shutter at same time intervals.

If each obtained image is divided into rectangular strips at intervals of 4/3 the grating period and a kth rectangular strip of a jth image is designated as Ijk, a first image I1 is divided into rectangular strips I11, I12, and I13; a second image is divided into I21, I22, and I23; and subsequent images are divided into Ij1, Ij2, and Ij3. If we consider a rectangular strip I(j−2)3, rectangular strip I(j−1)2, and rectangular strip Ij1, these images show same part of the measuring object 3 and the grating patterns projected on the images are phase-shifted from one another by $2\pi/3$.

The three images are exactly the same as the images produced by the ordinary grating projection phase shift method and shown in FIG. 4 except an X-direction width. That is, these images allow calculation based on the grating projection phase shift method to be performed for one rectangular strip. Then, each time one image is input, i.e., each time the measuring instrument scanning stage 2 moves 4/3 the grating period, the calculation based on the grating projection phase shift method is performed for one rectangular strip, making it possible to perform calculations one after another on a strip by strip basis. After all, if a table continues to be moved by a little more than a required size, measurement results of the desired size can be obtained without making step-and-repeat movements. The term "little more than" means allowance for the fact that j=1 to 2 cannot be calculated as well as for movements for acceleration and deceleration during a start or stop of the measuring instrument scanning stage 2.

In 4/3=1+1/3 the grating period, i.e., in the movement interval described above, 1/3 is important and corresponds to the phase shift amount $\phi=2\pi\times 1/3=2\pi/3$. The integer part may contain another positive integer value n rather than 1. Please note, in the case of the 3-step method, which requires at least three rectangular strips in one field of view, (n+1/3)×3 needs to be equal to or less than the total number P of grating lines in the field of view. That is, an integer which satisfies 0<=n<=(P−1)/3 is selected. With the N-step method, generally the movement interval is n+1/N (0<=n<=(P−1)/N). The fractional part 1/N does not necessarily have to be 1/N because basically it is sufficient if the initial phase of the sine wave can be determined, but a typical value will be 1/N.

The larger the number of steps N, the higher the accuracy. However, with an actual inspection apparatus which attaches importance to rapidity, 3-step method or 4-step method is used to take advantage of rapidity and efficiency which are features of the grating projection phase shift method. 4-step method which allows easy calculation and gives higher accuracy than 3-step method may be used most commonly.

However, in the present embodiment, a large number of steps do not necessarily lead to speed reduction. In the present embodiment, since the measuring instrument scanning stage 2 moves even during exposure time of the CMOS area sensor 9, blur occurs in resulting images. Therefore, the speed of the measuring instrument scanning stage 2 almost depends on a permissible amount of blur (an amount of movement during the exposure time) and a required amount of light. For example, if the exposure time is reduced, the speed of the measuring instrument scanning stage 2 can be increased, but if the exposure time is reduced too much, the amount of light will become insufficient. That is, the speed is determined based on the shortest exposure time which satisfies the amount of light and on the permissible amount of blur.

Once the speed of the measuring instrument scanning stage 2 is determined in the manner described above, the smallest width of the rectangular strip is determined from the smallest imaging interval of the CMOS area sensor 9. For example, when the exposure time is 0.1 ms and the permissible blur amount is one pixel or less and the smallest imaging interval of the CMOS area sensor 9 is 10 ms (100 fps), the width of the rectangular strip is 100 pixels at most. Even in the case of an 8-step method, the width of the rectangular strip is 800 pixels, which fit well in one field of view of recent high-speed, high-resolution cameras. The speed does not change even if the number of steps is four or six. Thus, in the present embodiment, it is rational to increase accuracy using larger multi-step phase shifting.

An important factor for success of this technique is timing of image acquisition. With the typical grating projection phase shift method, since the grating pattern rather than the measuring object 3 moves as shown in FIG. 4, positions on the measuring object 3 which are represented by coordinates match exactly among plural obtained images, while with the present embodiment the positions differ obviously. Errors occur unless corresponding pixels on the plural images shown in right side of FIG. 5 accurately represent same positions on the measuring object 3. It is necessary to acquire images accurately at targeted positions. Therefore, in the present embodiment, the measuring instrument scanning stage 2 is equipped with the linear encoder 13. For example, by using a linear encoder 13 with a sufficiently high resolution commensurate with a pixel resolution (field-of-view size in the X direction divided by the number of pixels in the X direction) of the image, counting an encoder signal in real time, and configuring an electronic circuit so as to output a trigger signal to the CMOS area sensor 9 at a targeted count value, it is possible to obtain an image at a targeted position.

Another technique may be used as long as images can be acquired accurately at targeted positions. If the measuring instrument scanning stage 2 can be controlled so as to perform uniform motion accurately, the grating projection phase shift method can be implemented using an accurate timer without relying on an encoder.

Besides, performance of the image forming lens 10 also presents a problem. If the image forming lens 10 is subject to distortion aberration, it is likely that pixels will not match correctly. Also, image forming performance needs to be as uniform as possible in the field of view.

As described above, compared to the light section method, the grating projection phase shift method can increase efficiency and speed of the apparatus as a whole. That is, lots of data can be obtained using a smaller number of images. Also, it can be said that calculation of the initial phase is made higher in reliability because the initial phase can be calculated solely from data on certain coordinate values alone (without the need for information on adjacent pixels), keeping it from affecting the calculation (in principle) the local differences in reflectance or undulation on surfaces of the object. Also, since the measuring object is fixed during continuous scanning, high-definition operation is not required of a transfer mechanism for the stage configured to carry the measuring object and there is no need to consider micromotion of the measuring object during the continuous scanning. Therefore, the stage used to carry the measuring object can be configured simply and the measuring object can be replaced easily and simply using the loader 705, unloader 706, and the like.

Although a method for calculating the initial phase has been described above, the present embodiment is not limited to this technique. There are also calculations for determining the initial phase other than the arithmetic expression described above. Besides, although a grating pattern is assumed to be a sinusoidal pattern, another periodic pattern may be used. For example, even if only an imperfect sinusoidal pattern (e.g., a blurred binary grating pattern) is available, as long as the sinusoidal pattern has a precise periodicity, the initial phase can be determined if a relationship between phase and intensity distribution is described in advance using, for example, an LUT (look-up table). In any case, as long as that amount of the periodic pattern which corresponds to the initial phase can be determined, the present invention is applicable.

Next, an embodiment of the present invention which implements a method for performing some different measurements and inspections simultaneously will be described with reference to FIG. 6.

As described earlier, measuring speed of a continuous scan type measuring instrument which uses a two-dimensional image sensing device such as the CMOS area sensor 9 is constrained mainly by the amount of light and exposure time. When a high-speed (high frame rate) CMOS area sensor 9 is used, it is highly likely that a speed margin is available, i.e., there is no need for using the highest frame rate. By utilizing the margin, it is possible to perform other measurements simultaneously.

Figure 6:
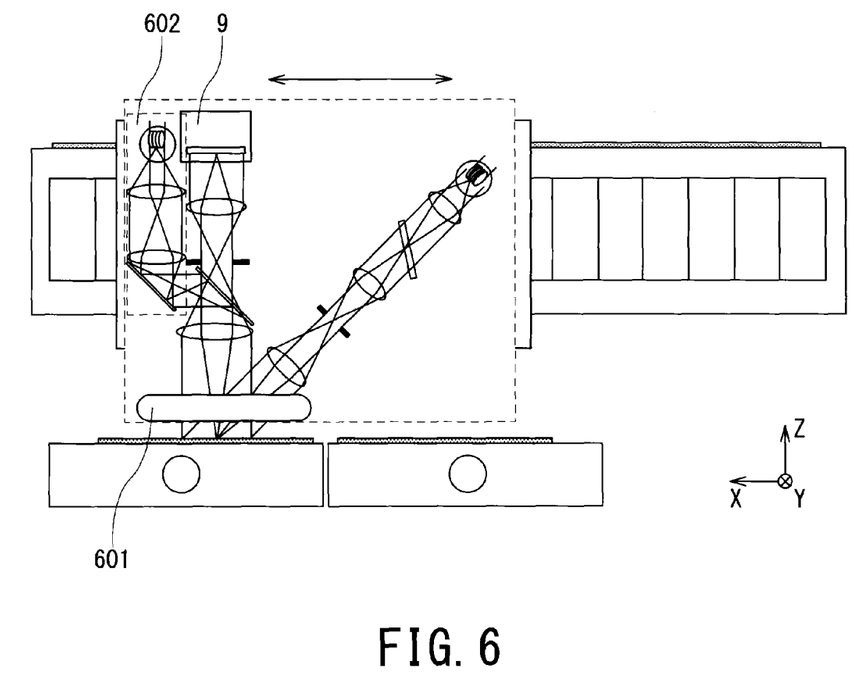
FIG. 6 is an explanatory diagram for describing an example of a method of implementing plural measurements simultaneously.

FIG. 6 shows ring illumination 601 and vertical epi-illumination 602 of a TTL (Through The Lens) mode added to a surface shape measuring instrument based on the grating projection phase shift method. These illuminations are so-called strobe illuminators capable of instantaneous light emission.

If a maximum frame rate of the CMOS area sensor 9 is P fps (frame per second) and a frame rate necessary for the grating projection phase shift method is P/2 fps, images irrelevant to the grating projection phase shift method can be acquired while images are acquired by the grating projection phase shift method.

The grating projection phase shift method requires more than two times of image sensing to obtain one field of view of data, but it is not always necessary to obtain plural images from one field of view, for example, in the case of dimensional measurements of an object in a planar direction, reading of characters, or defect inspection. That is, for such measurement or inspection, it is sufficient to acquire one image while three images (for example) are acquired by the grating projection phase shift method.

If the maximum frame rate of the CMOS area sensor 9 is a multiple of that of the grating projection phase shift method as described above, since a multiple of images can be obtained while images are obtained from one field of view by the grating projection phase shift method, a 3-step phase shift method, for example, can acquire images under the ring illumination 601, images under the vertical epi-illumination 602, or images under both the illuminations meanwhile. Therefore, the ring illumination 601 and vertical epi-illumination 602 can further increase efficiency and speed of the apparatus as a whole. Also, the continuous scan type measuring apparatus 100 according to the present embodiment can implement a more efficient reliable continuous scan type surface shape measurement than the light section method and can practically eliminate wasted time caused by a product replacement during which the apparatus is down. This makes it possible to increase efficiency and speed of the apparatus as a whole. Thus, it is believed that there is especially great demand for this in the semiconductor industry which requires high-speed, high-accuracy, complicated measurements and inspections.

Also, regarding bump inspection on the substrate, not only height measurement of bumps, but also dimensional measurement in a planar direction such as bump diameter measurement is often required. In this regard, the continuous scan type measuring apparatus 100 equipped with the optical application measuring instrument 1 as a surface shape measuring instrument of the continuous scan type can take dimensional measurements in the planar direction as well as measurements of surface shape by continuous scanning type.

While certain embodiments have been described, these embodiments have been presented by way of example only, and are not intended to limit the scope of the invention. Indeed, the novel embodiments described herein may be embodied in a variety of other forms; furthermore, various omissions, substitutions and changes in the form of the embodiments described herein may be made without departing from the scope of the invention as defined by the appended claims. The accompanying claims and their equivalents are intended to cover such forms or modifications as would fall within the scope of the invention as defined by the appended claims.

The invention claimed is:

1. A continuous scan type measuring apparatus comprising:
    an optical application measuring instrument configured to perform a surface shape measurement of a measuring object;
    a single-axis measuring instrument scanning stage configured to carry the optical application measuring instrument, causing the optical application measuring instrument to perform continuous scanning along a predetermined direction; and two carrier stages configured to detachably mount respective measuring objects thereon and configured to move independently of each other, wherein the two carrier stages are positioned independently at one of a measurement position of the optical application measuring instrument and a replacement position of the measuring objects, and a carrier stage, which is at the measurement position and on which the measuring object subjected to the surface shape measurement is mounted, is fixed during the continuous scanning, the optical application measuring instrument performs, while the measuring object which has been measured is being replaced with a next measuring object with one of the two carrier stages positioned at the replacement position, the surface shape measurement of the measuring object on an other of the two carrier stages positioned at the measurement position, the single-axis measuring instrument scanning stage causes the optical application measuring instrument to perform continuous scans repeatedly along the predetermined direction at intervals of a predetermined waiting time when a measurement width covered by the optical application measuring instrument in an orthogonal direction to the predetermined direction is smaller than a width of the measuring object in the orthogonal direction, and when the continuous scans are performed repeatedly, the carrier stage, which is at the measurement position and on which the measuring object subjected to the surface shape measurement is mounted, is fixed during a time of the continuous scanning, and moves, during the predetermined waiting time, in the orthogonal direction by a width equal to or smaller than the measurement width in the orthogonal direction.

2. The continuous scan type measuring apparatus according to claim 1, wherein the single-axis measuring instrument scanning stage causes the optical application measuring instrument to scan continuously in a predetermined orientation along the predetermined direction and then causes the optical application measuring instrument to scan in an orientation opposite the predetermined orientation after the predetermined waiting time.

3. The continuous scan type measuring apparatus according to claim 2, wherein the optical application measuring instrument is a grating projection type surface shape measuring instrument including an image input system and an image processing apparatus, the image input system including an image sensing unit and a grating projection unit, the image sensing unit including a two-dimensional image sensing device and an image forming unit, the two-dimensional image sensing device formed by a two-dimensional arrangement of electromagnetic wave-electricity conversion elements configured to convert an electromagnetic wave into an electrical signal, and the image forming unit forming an image of the measuring object on a conversion plane of the two-dimensional image sensing device, and the grating projection unit configured to project a grating-shaped shading pattern onto the measuring object at an angle different from an image sensing direction of the image sensing unit, and the image processing apparatus configured to process an image signal from the image input system, wherein the grating projection type surface shape measuring instrument is carried by the measuring instrument scanning stage configured to move in the predetermined direction, the predetermined direction being parallel to a plane which contains an optical axis of the grating projection unit and an optical axis of the image sensing unit, and the surface shape measurement of the measuring object is performed by acquiring an image, without stopping the measuring instrument scanning stage, each time the measuring instrument scanning stage moves a fixed distance, by using at least three consecutive images, and by determining an initial phase of a grating pattern for each pixel in common regions of the measuring object picked up in the at least three consecutive images.

4. The continuous scan type measuring apparatus according to claim 3, wherein the grating projection type surface shape measuring instrument further includes a ring-shaped instantaneous illuminator at a tip of the image forming unit, and acquires an image by instantaneously illuminating and exposing the measuring object while images are acquired at fixed intervals for the surface shape measurement.

5. The continuous scan type measuring apparatus according to claim 4, wherein the grating projection type surface shape measuring instrument further includes a coaxial epi-illuminator for instantaneous illumination in a direction of an optical axis of the image forming unit, and acquires the image by instantaneously illuminating and exposing the measuring object while the images are acquired at the fixed intervals for the surface shape measurement.

6. The continuous scan type measuring apparatus according to claim 3, wherein the grating projection type surface shape measuring instrument further includes a coaxial epi-illuminator for instantaneous illumination in a direction of an optical axis of the image forming unit, and acquires an image by instantaneously illuminating and exposing the measuring object while images are acquired at fixed intervals for the surface shape measurement.

7. The continuous scan type measuring apparatus according to claim 1, wherein:

the optical application measuring instrument is a grating projection type surface shape measuring instrument including an image input system and an image processing apparatus, the image input system including an image sensing unit and a grating projection unit, the image sensing unit including a two-dimensional image sensing device and an image forming unit, the two-dimensional image sensing device formed by a two-dimensional arrangement of electromagnetic wave-electricity conversion elements configured to convert an electromagnetic wave into an electrical signal, and the image forming unit forming an image of the measuring object on a conversion plane of the two-dimensional image sensing device, and the grating projection unit configured to project a grating-shaped shading pattern onto the measuring object at an angle different from an image sensing direction of the image sensing unit, and the image processing apparatus configured to process an image signal from the image input system, wherein the grating projection type surface shape measuring instrument is carried by the measuring instrument scanning stage configured to move in the predetermined direction, the predetermined direction being parallel to a plane which contains an optical axis of the grating projection unit and an optical axis of the image sensing unit, and the surface shape measurement of the measuring object is performed by acquiring an image, without stopping the measuring instrument scanning stage, each time the measuring instrument scanning stage moves a fixed distance, by using at least three consecutive images, and by determining an initial phase of a grating pattern for each pixel in common regions of the measuring object picked up in the at least three consecutive images.

8. The continuous scan type measuring apparatus according to claim 7, wherein the grating projection type surface shape measuring instrument further includes a ring-shaped instantaneous illuminator at a tip of the image forming unit, and acquires an image by instantaneously illuminating and exposing the measuring object while images are acquired at fixed intervals for the surface shape measurement.

9. The continuous scan type measuring apparatus according to claim 8, wherein the grating projection type surface shape measuring instrument further includes a coaxial epi-illuminator for instantaneous illumination in a direction of an optical axis of the image forming unit, and acquires the image by instantaneously illuminating and exposing the measuring object while the images are acquired at the fixed intervals for the surface shape measurement.

10. The continuous scan type measuring apparatus according to claim 7, wherein the grating projection type surface shape measuring instrument further includes a coaxial epi-illuminator for instantaneous illumination in a direction of an optical axis of the image forming unit, and acquires an image by instantaneously illuminating and exposing the measuring object while images are acquired at fixed intervals for the surface shape measurement.

11. The continuous scan type measuring apparatus according to claim 1, wherein the two carrier stages are positioned at respective different measurement positions, each of which is located along the predetermined direction and placed within a scanning range of the optical application measuring instrument in the predetermined direction, the one of the two carrier stages, on which the next measuring object after replacement is mounted at the replacement position, moves to and is positioned at a measurement position of the one of the two carrier stages before the surface shape measurement of the measuring object mounted on the other of the two carrier stages is finished, and after the surface shape measurement of the measuring object mounted on the other of the two carrier stages is finished, the measuring instrument scanning stage moves from a measurement position of the other of the two carrier stages to the measurement position of the one of the two carrier stages along the predetermined direction and causes, without stopping, the optical application measuring instrument to start the surface shape measurement of the measuring object mounted on the one of the two carrier stages.

12. The continuous scan type measuring apparatus according to claim 11, wherein:

the optical application measuring instrument is a grating projection type surface shape measuring instrument including an image input system and an image processing apparatus, the image input system including an image sensing unit and a grating projection unit, the image sensing unit including a two-dimensional image sensing device and an image forming unit, the two-dimensional image sensing device formed by a two-dimensional arrangement of electromagnetic wave-electricity conversion elements configured to convert an electromagnetic wave into an electrical signal, and the image forming unit forming an image of the measuring object on a conversion plane of the two-dimensional image sensing device, and the grating projection unit configured to project a grating-shaped shading pattern onto the measuring object at an angle different from an image sensing direction of the image sensing unit, and the image processing apparatus configured to process an image signal from the image input system, wherein the grating projection type surface shape measuring instrument is carried by the measuring instrument scanning stage configured to move in the predetermined direction, the predetermined direction being parallel to a plane which contains an optical axis of the grating projection unit and an optical axis of the image sensing unit, and the surface shape measurement of the measuring object is performed by acquiring an image, without stopping the measuring instrument scanning stage, each time the measuring instrument scanning stage moves a fixed distance, by using at least three consecutive images, and by determining an initial phase of a grating pattern for each pixel in common regions of the measuring object picked up in the at least three consecutive images.

13. The continuous scan type measuring apparatus according to claim 12, wherein the grating projection type surface shape measuring instrument further includes a ring-shaped instantaneous illuminator at a tip of the image forming unit, and acquires an image by instantaneously illuminating and exposing the measuring object while images are acquired at fixed intervals for the surface shape measurement.

14. The continuous scan type measuring apparatus according to claim 13, wherein the grating projection type surface shape measuring instrument further includes a coaxial epi-illuminator for instantaneous illumination in a direction of an optical axis of the image forming unit, and acquires the image by instantaneously illuminating and exposing the measuring object while the images are acquired at the fixed intervals for the surface shape measurement.

15. The continuous scan type measuring apparatus according to claim 12, wherein the grating projection type surface shape measuring instrument further includes a coaxial epi-illuminator for instantaneous illumination in a direction of an optical axis of the image forming unit, and acquires an image by instantaneously illuminating and exposing the measuring object while images are acquired at fixed intervals for the surface shape measurement.

* * * * *